United States Patent
Obrebski

(10) Patent No.: US 7,335,223 B2
(45) Date of Patent: Feb. 26, 2008

(54) APPARATUS FOR THE TREATMENT OF BODY TISSUE

(75) Inventor: Andreas Obrebski, Düsseldorf (DE)

(73) Assignee: Carl-Zeiss-Stiftung (DE)

(*) Notice: Subject to any disclaimer, the term of this patent is extended or adjusted under 35 U.S.C. 154(b) by 40 days.

(21) Appl. No.: 10/768,477

(22) Filed: Jan. 29, 2004

(65) Prior Publication Data
US 2004/0230186 A1 Nov. 18, 2004

(30) Foreign Application Priority Data
Jan. 30, 2003 (DE) ................. 103 04 221

(51) Int. Cl.
*A61B 18/18* (2006.01)
(52) U.S. Cl. ................. 609/9; 606/1; 607/88
(58) Field of Classification Search ......... 128/898; 606/9
See application file for complete search history.

(56) References Cited

U.S. PATENT DOCUMENTS

| | | | | |
|---|---|---|---|---|
| 4,737,628 A | * | 4/1988 | Lovoi | 606/12 |
| 5,104,392 A | * | 4/1992 | Kittrell et al. | 606/15 |
| 5,452,723 A | * | 9/1995 | Wu et al. | 600/342 |
| 5,571,083 A | * | 11/1996 | Lemelson | 604/522 |
| 5,707,369 A | | 1/1998 | Vaitekunas et al. | |
| 5,745,545 A | * | 4/1998 | Hughes | 378/65 |
| 5,823,993 A | * | 10/1998 | Lemelson | 604/503 |
| 5,846,236 A | | 12/1998 | Lindenmeier et al. | |
| 5,871,018 A | * | 2/1999 | Delp et al. | 128/898 |
| 5,944,748 A | * | 8/1999 | Mager et al. | 607/88 |
| 6,022,347 A | | 2/2000 | Lindenmeier et al. | |
| 6,386,758 B2 | * | 5/2002 | Loser | 378/205 |
| 6,690,966 B1 | * | 2/2004 | Rava et al. | 600/473 |
| 2002/0023652 A1 | * | 2/2002 | Riaziat et al. | 128/897 |
| 2003/0060810 A1 | * | 3/2003 | Syrowicz et al. | 606/9 |
| 2004/0002641 A1 | * | 1/2004 | Sjogren et al. | 600/407 |
| 2004/0082940 A1 | * | 4/2004 | Black et al. | 606/9 |
| 2005/0149012 A1 | * | 7/2005 | Penny et al. | 606/41 |

FOREIGN PATENT DOCUMENTS

| | | |
|---|---|---|
| JP | 5-49644 | 3/1993 |
| JP | 2002-17751 | 1/2002 |

\* cited by examiner

*Primary Examiner*—Henry M. Johnson, III
(74) *Attorney, Agent, or Firm*—Gerald E. Hespos; Anthony J. Casella

(57) ABSTRACT

An apparatus for treating body tissue includes a treatment instrument 1 for treating the body tissue and a measuring unit 3 for measuring the actual value of a parameter of the body tissue at at least one measuring point. An identifier 4 is connected to the measuring unit 3 for identifying the body tissue to be treated on the basis of the actual value and for outputting a coordinate signal containing the coordinates of the body tissue to be treated. A positioning device 2 receives the coordinate signal and moves the treatment instrument 1 to the body tissue to be treated. An updating device 8 is connected to the measuring unit 3 and the identifier 4 and outputs an updating signal for triggering renewed measurement of the actual value and renewed identification of body tissue to be treated.

10 Claims, 4 Drawing Sheets

APPARATUS FOR THE TREATMENT OF BODY TISSUE

BACKGROUND OF THE INVENTION

1. Field of the Invention

The present invention concerns an apparatus for the treatment and in particular for the removal of body tissue.

2. Description of the Related Art

A main area of use of apparatuses for the treatment of body tissue involves surgery, for example for the treatment of cancerous ulcers and growths, tattoos, age spots and so forth. In addition however they are also used in dental treatments, for example for the removal of caries, or in cosmetic treatments, for example for the removal of hairs.

Frequently the above-mentioned treatments are carried out manually, that is to say the doctor performing the treatment removes for example a tumour using a scalpel after he has evaluated the results of an identification or visualisation procedure. In that situation it can happen that parts of the unhealthy body tissue are overlooked and therefore the tumour is not completely removed. On the other hand it can also happen that an unnecessarily large amount of body tissue is removed, particularly if, from the point of view of the doctor performing the treatment, the unhealthy body tissue can visually only be distinguished with difficulty from healthy body tissue. The problems referred to are particularly apparent if the body tissue to be removed is distributed in a flat and in particular thin flat configuration or in thread form in the healthy body tissue. An operation is then particularly long and requires a high level of concentration from the doctor throughout the entire duration of the operation. It is therefore taxing and tiring for the doctor. Similar problems also arise with other forms of treatment than the removal of body tissue.

The state of the art discloses operation navigational systems which make the operation easier for the doctor insofar as they provide him with prepared items of information about the area of the operation and/or the further course of the operation.

JP 05049644 A describes for example a navigation system in which a planning unit simulates the operation on the basis of previously recorded image data and produces therefrom an operation plan in which the position, size and state of a diseased change in tissue are taken into account. In the course of the operation the simulated data are passed step by step to a navigation control system which delivers instructions for the further progress of the operation.

JP 2002017751 A describes an operation navigation apparatus in which detailed information obtained by means of a tomogram about the tissue in the area around the operating instrument is represented on a display.

In comparison with that state of the art, the object of the present invention is to provide an apparatus for the treatment of body tissue, which further facilitates the operating procedure for the doctor performing the treatment.

SUMMARY OF THE INVENTION

An apparatus according to the invention for the treatment of body tissue includes:
- a treatment instrument for the treatment of body tissue;
- a measuring unit for measuring the actual value of a parameter of the body tissue at at least one measurement point of the body tissue;
- an identifier connected to the measuring unit for identifying the body tissue to be treated on the basis of the actual value and for outputting a co-ordinate signal containing the co-ordinates of the body tissue to be treated;
- a positioning device connected to the identifier for receiving the co-ordinate signal for moving to the body tissue to be treated with the treatment instrument on the basis of the co-ordinate signal;
- an activator for activating the treatment instrument; and
- an updating device which is connected to the measuring unit and the identifier and which is adapted to output an updating signal for triggering renewed measurement of the actual value and renewed identification of body tissue to be treated.

In this respect the term treatment is used to denote for example the removal, radiation treatment or bleaching of body tissue.

The apparatus according to the invention for the treatment of body tissue is based on the idea of identifying the body tissue to be treated on the basis of a parameter which is to be repeatedly measured and which is taken for example from an online recognition method, establishing the co-ordinates of the body tissue identified in that way, and using those co-ordinates for automated positioning of the treatment instrument. As long as body tissue to be treated is to be identified, the treatment instrument, for example a laser or a pulse bipolar plasma scalpel (Pulsed Electron Avalanche Knife—PEAK) is kept active, that is to say at least in readiness, so that the doctor can use it or enable the treatment. Treatment of the body tissue however can also be effected automatically without separate enablement by the doctor. The treatment is preferably effected until no more body tissue to be treated is to be identified.

If enablement of the treatment instrument by the doctor is wanted or if it is required for example in consideration of statutory provisions, the apparatus for the treatment of body tissue can be provided with an enablement device for enablement of the treatment instrument.

An advantage of the apparatus according to the invention is that the doctor only has to set up the apparatus and monitor and possibly enable the actual operation, which permits him to work ergonomically. A further advantage is the precision in the treatment. Only the tissue to be treated is treated, for example subjected to radiation treatment; the healthy tissue is preserved. In addition the treatment duration can be reduced, by virtue of the precision in terms of automated positioning. The apparatus according to the invention therefore reduces on the one hand the stress imposed on the doctor and on the other hand the patient stress, the latter in particular also due to the possible reduction in the length of the treatment time. The effectiveness of the treatment is increased overall and costs are reduced or the profit margin enhanced.

In an embodiment of the invention the identifier includes a memory for storing at least one reference value of the parameter and a comparison device connected to the memory and the measuring unit for comparing the actual value to the at least one reference value. In this embodiment the identifier outputs the co-ordinate signal if the comparison of the actual value with the reference value produces a predetermined result. In this respect, the reference value is also to be interpreted as a range of values in which the actual value is or is not intended to lie so that the corresponding tissue is identified as tissue to be treated.

The online recognition signal for diseased tissue (for example cancer, caries etc.) of an online/inline recognition method can be used as the reference value which represents the control parameter of a regulating circuit. As long as the online recognition signal, that is to say the reference value, is measured as the actual value, the treatment instrument is kept in readiness. The online/inline recognition methods which can be used are for example methods based on fluorescence, optical coherence tomography (Optical Coherence Tomography, OCT), inline microscopy or optical imaging with various threshold values in respect of colour and/or intensity.

In a further embodiment of the apparatus the comparison device is adapted for the output of an identification signal identifying the body tissue to be treated. In addition the identifier includes a co-ordinate detection unit connected to the comparison device for receiving the identification signal, for detecting the co-ordinates of the tissue to be treated upon reception of the identification signal and for outputting the co-ordinate signal to the positioning device.

In particular the co-ordinate detection unit can be adapted for emitting a plurality of co-ordinates respectively representing body tissue to be treated, in a single co-ordinate signal. The positioning device is then adapted for subsequently moving to the co-ordinates of the co-ordinate signal. That configuration affords the possibility of firstly concluding identification of the body tissue to be treated, in a given region of the body, before beginning with the treatment procedure, that is to say for example radiation treatment or removal, of the tissue in question.

Advantageously the apparatus according to the invention includes a matching device for matching the co-ordinate systems of the body tissue to be treated and the treatment instrument. It is particularly advantageous if the updating device is also connected to the matching device for the delivery of a matching signal for triggering the co-ordinate matching procedure. In particular the repeated matching step during the operation makes it possible to obviate a reduction in the degree of precision in positioning by virtue of displacements of the two co-ordinate systems relative to each other.

In a further development of the invention the treatment instrument is adapted to deliver treatment energy in pulse form. In addition the updating device includes at least one counter for counting the pulses and is designed in such a way that it outputs an updating signal and/or the matching signal after a given number of pulses. By predetermining the number of pulses, after which an updating or matching step is to be effected, it is possible in that way to adjust the frequency of the updating procedures or the matching procedure.

Further features, properties and advantages of the present invention are described hereinafter by means of an embodiment by way of example with reference to the accompanying drawings.

DETAILED DESCRIPTION OF THE PREFERRED EMBODIMENTS

Figure 1:
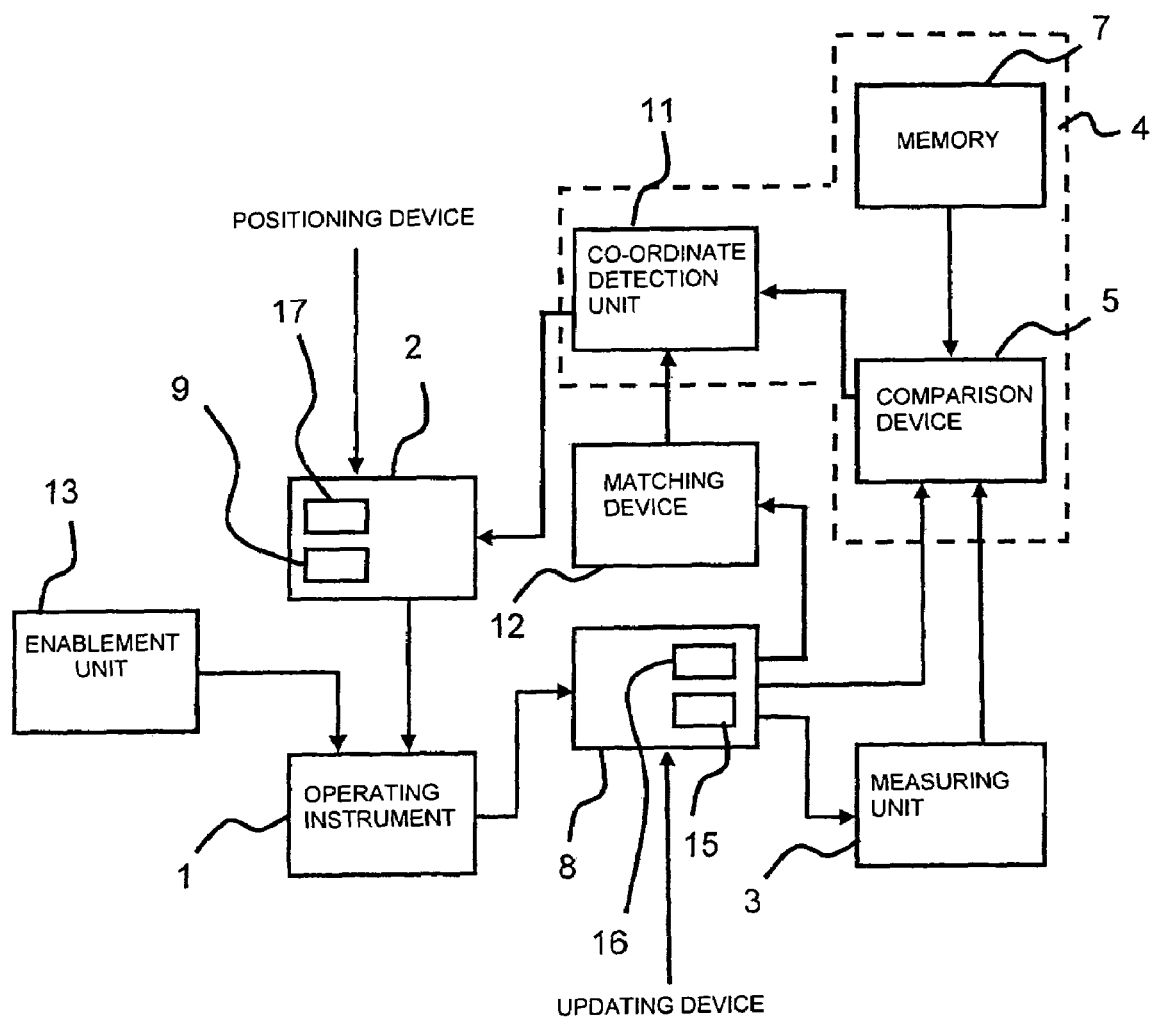
FIG. 1 shows an embodiment of the apparatus according to the invention for the treatment of body tissue, by means of a block circuit diagram.

FIG. 1 shows a block circuit diagram of the apparatus according to the invention for the treatment of body tissue. The apparatus of the illustrated embodiment is in the form of an apparatus for the removal of body tissue and includes as the treatment or operating instrument 1 a laser which is mounted on a positioning device 2 and as a measuring unit 3 for measuring the actual value of a parameter of the body tissue a device for optical coherence tomography (Optical Coherence Tomography, OCT). The measuring unit 3 is connected for the transmission of the actual value to a comparator as a comparison device 5 which in turn is connected to a memory 7 containing at least one reference value in respect of the parameter. Also connected to the measuring unit 3 and the comparison device 5 is an updating device 8 which is adapted to output an updating signal.

The apparatus for the treatment or removal of body tissue further includes a co-ordinate detection unit 11 which is connected to the comparison device 5 and the positioning device 2. The comparison device 5, the memory 7 and the co-ordinate detection unit 11 together form an identifier 4 for identifying body tissue to be removed and for outputting a co-ordinate signal containing the co-ordinates of the body tissue to be removed.

In addition, in the present embodiment, an activating device 9 for activating the operating instrument 1 is integrated into the positioning device 2. The activating device 9 however can also be arranged outside the positioning device. Optionally, an enablement unit 13, for example a foot or hand switch, can also be connected to the operating instrument 1, by means of which the activated operating instrument 1 and therewith the treatment can be enabled by the doctor. Advantageously the arrangement also has a matching device 12 for matching the co-ordinate systems in which the position of a part of the body and the operating instrument respectively are ascertained.

The function of the comparison device 5 is to identify body tissue to be removed, for example tumour tissue, on the basis of the actual value of the parameter, which is measured by the measuring unit 3. For that purpose, the comparison device 5 performs a comparison of the measurement signal transmitted by the measuring unit 3 to the online recognition signal stored in the memory 7 for the tissue to be removed (reference value). If the online recognition signal and the measuring signal are identical then body tissue to be removed is at the measuring location at which the measuring unit 3 recorded the measuring signal. In that case the comparison device 5 outputs an identification signal to the co-ordinate detection unit 11 in order to trigger detection of the co-ordinates of the corresponding measuring point.

When the co-ordinate detection procedure is concluded the co-ordinate detection unit 11 outputs a co-ordinate signal containing the co-ordinates of the body tissue to be removed, to the positioning device 2 which approaches the first ordinates transmitted with the co-ordinate signal, with the operating instrument 1, and activates the operating instrument 1. Removal of the body tissue at those co-ordinates is now effected automatically or after enablement by the doctor by means of a laser pulse or a plurality of laser pulses. For the purposes of counting the laser pulses delivered, in the present embodiment the updating device 8 includes a counter 15 connected to the laser 1, in particular to the control system of the laser 1. Unlike the situation described in the illustrated embodiment, the counter 15 can also be arranged outside the updating device 8 and can be in signal communication therewith.

After the delivery of a predetermined number of laser pulses the positioning device 2 moves to the next co-ordinates. As soon as all parts of the body represented by co-ordinates have been treated, the counter has reached a given counter condition which triggers the output of the updating signal by the updating device 8, whereupon fresh measurement of the actual value of the body tissue parameter and fresh comparison with the reference value are implemented. If the renewed comparison operation reveals that there is still further body tissue to be removed, renewed output of a co-ordinate signal is effected.

Optionally, the updating device 8 may include a second counter 16 which, when a predetermined counter condition is reached, effects matching of the co-ordinate systems of the operating instrument 1 and the tissue region to be treated. In that case the updating device 8 is also connected to the matching device 12, for the delivery of an updating signal. Like the first counter 15 the second counter 16 may also be arranged outside the updating device 8 and may be in signal communication therewith. Output of the updating signal and output of the matching signal can also be effected by means of two separate updating devices.

It should be pointed out at this juncture that the co-ordinate signal only needs to include one set of co-ordinates. For example, when the comparison device 5 has identified a first measuring point with body tissue to be removed, a co-ordinate signal can be outputted and the laser 1 can be moved to the corresponding part of the body. After the delivery of a predetermined number of laser pulses updating of the measurement and the comparison is effected, and possibly further treatment of the same part of the body with laser pulses. It is only when the comparison operation shows that there is no longer any body tissue to be removed at that part of the body that the actual value is measured at the next part of the body.

Figure 2:
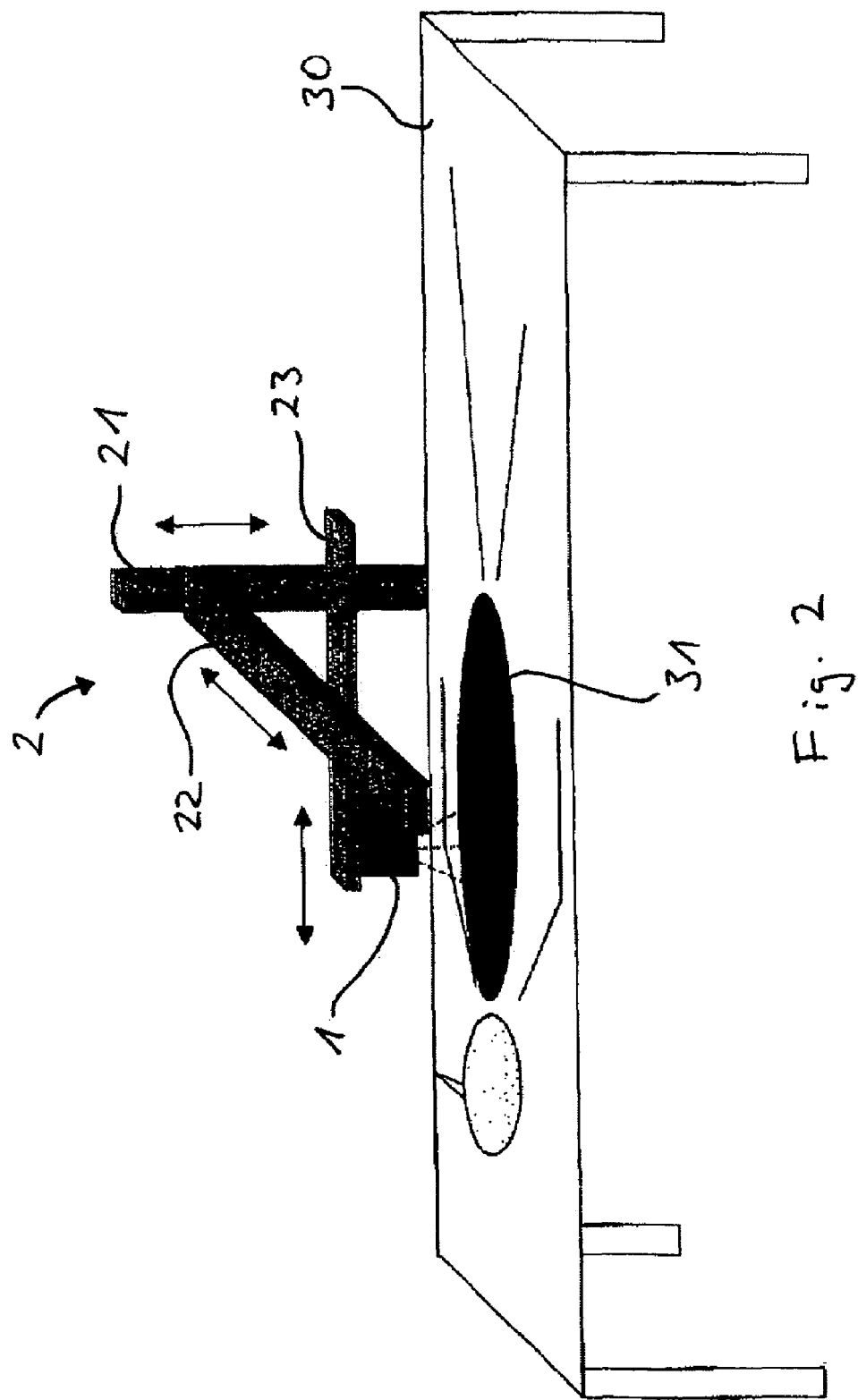
FIG. 2 is a diagrammatic view showing an example of a positioning device which can be used in the present invention.

FIG. 2 diagrammatically shows a simple example of the design configuration of a positioning device 2 which can be used in the present invention. The Figure also shows a patient 31 lying on an operating table 30.

The positioning device 2 includes a stationary support stand 21 to which a first rail 22 is vertically displaceably secured. Mounted in turn to the first rail 22 is a second rail 23 which is displaceable horizontally in a first direction and on which the laser 1 is arranged displaceably in a second horizontal direction. The directions in which the rails 22, 23 and the laser 1 can be displaced are indicated by arrows in FIG. 2. In addition the laser 1 is preferably so fixed to the second rail 23 that a pivotal movement of the laser 1 is possible.

The positioning device 2 which is to be used in the apparatus according to the invention is however not limited to the configuration described with reference to FIG. 2. Rather, the treatment or operating instrument 1 can basically be mounted to any positioning device which affords degrees of freedom, sufficient for the intended treatment, for positioning of the treatment instrument 1.

Figure 3:
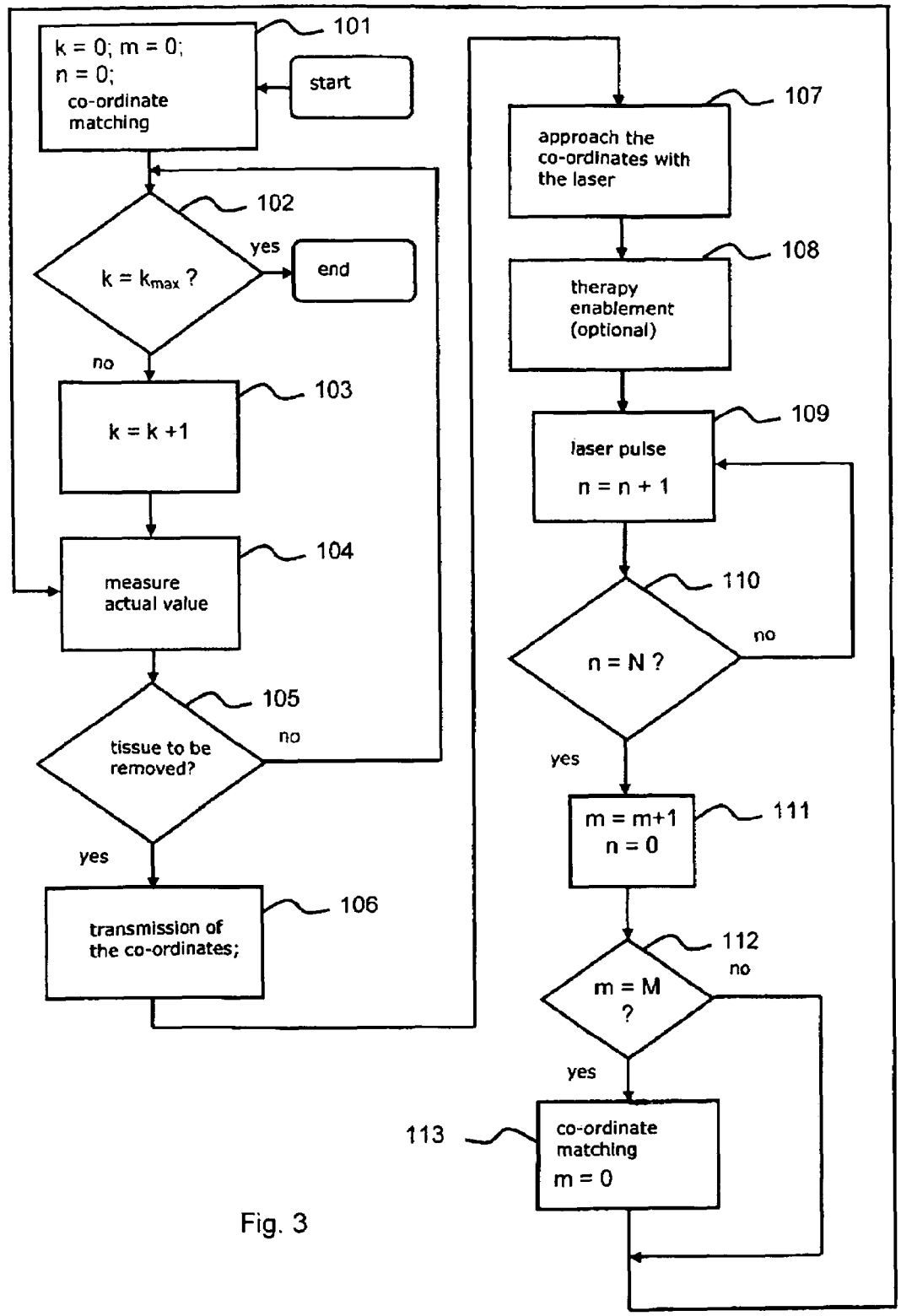
FIG. 3 shows a first possible procedure for effecting treatment with the apparatus according to the invention by means of a flow chart.

A first possible procedure for a treatment with the apparatus according to the invention for the treatment of body tissue is set forth hereinafter with reference to the flow chart of FIG. 3, in regard to the removal of body tissue. In the procedure hereinafter the actual value in respect of the body tissue is measured in a region of the body which is represented by k measuring points.

At the beginning of the treatment, an initialisation step 101 is effected, in which the co-ordinate system of the treatment or operating instrument is matched to that of the patient and all relevant parameters are set to a start value.

Step 102 involves querying whether the actual value has been measured at all k measuring points. If that is the case the treatment is concluded, If that is not the case k is increased by one (step 103) and the actual value in respect of the parameter is measured in step 104. In step 105 the identifier checks whether tissue to be removed is to be found at the k+1-th measuring point. If the result is negative the apparatus returns to step 102 and steps 102 to 105 are executed again.

If body tissue to be removed is identified at the k+1-th measuring point, then in step 106 the co-ordinates of the measuring point are transmitted to the positioning device 2 and those co-ordinates are then approached with the operating instrument 1 in step 107. An optional step 108 is then performed, in which the doctor enables the treatment. Thereafter the treatment is effected with a first laser pulse in step 109. In addition, the first counting parameter n which counts the number of laser pulses delivered is increased by one. The next step 110 involves checking whether a predetermined number N of laser pulses has already been delivered. If that is not the case, the apparatus returns to step 109, it delivers a further laser pulse, and it increases the counting parameter n by one. When the predetermined number N of laser pulses is reached, then in step 111 the first counting parameter n is reset to zero and a second counting parameter m which counts how often N laser pulses have already been delivered is increased by one. If in the subsequent step 112 it is detected that the second counting parameter has reached a predetermined value M, then step 113 involves renewed matching of the co-ordinate system of the operating instrument 1 with that of the patient. If it is detected in step 112 that the predetermined value M has not yet been reached, then step 113 is omitted.

Subsequently to step 112 or step 113 the apparatus at any event returns to step 104 in which the actual value of the portion of tissue which has just been treated and which is represented by the k+1-th measuring point is measured again. If tissue which still has to be removed is still identified in step 105, a renewed treatment is effected in accordance with steps 106 to 112 and 113 respectively. That is repeated until the identifier 4 no longer identifies any tissue to be removed.

As soon as the identifier 4 no longer identifies tissue to be removed, the apparatus goes back to step 102 and checks whether all measuring points have already been processed, that is to say whether k has reached the value $k_{max}$. If not, the apparatus advances to the next measuring point, if yes, there is no longer any tissue to be removed, in the whole of the treated region of tissue. The apparatus then terminates the treatment.

Figure 4:
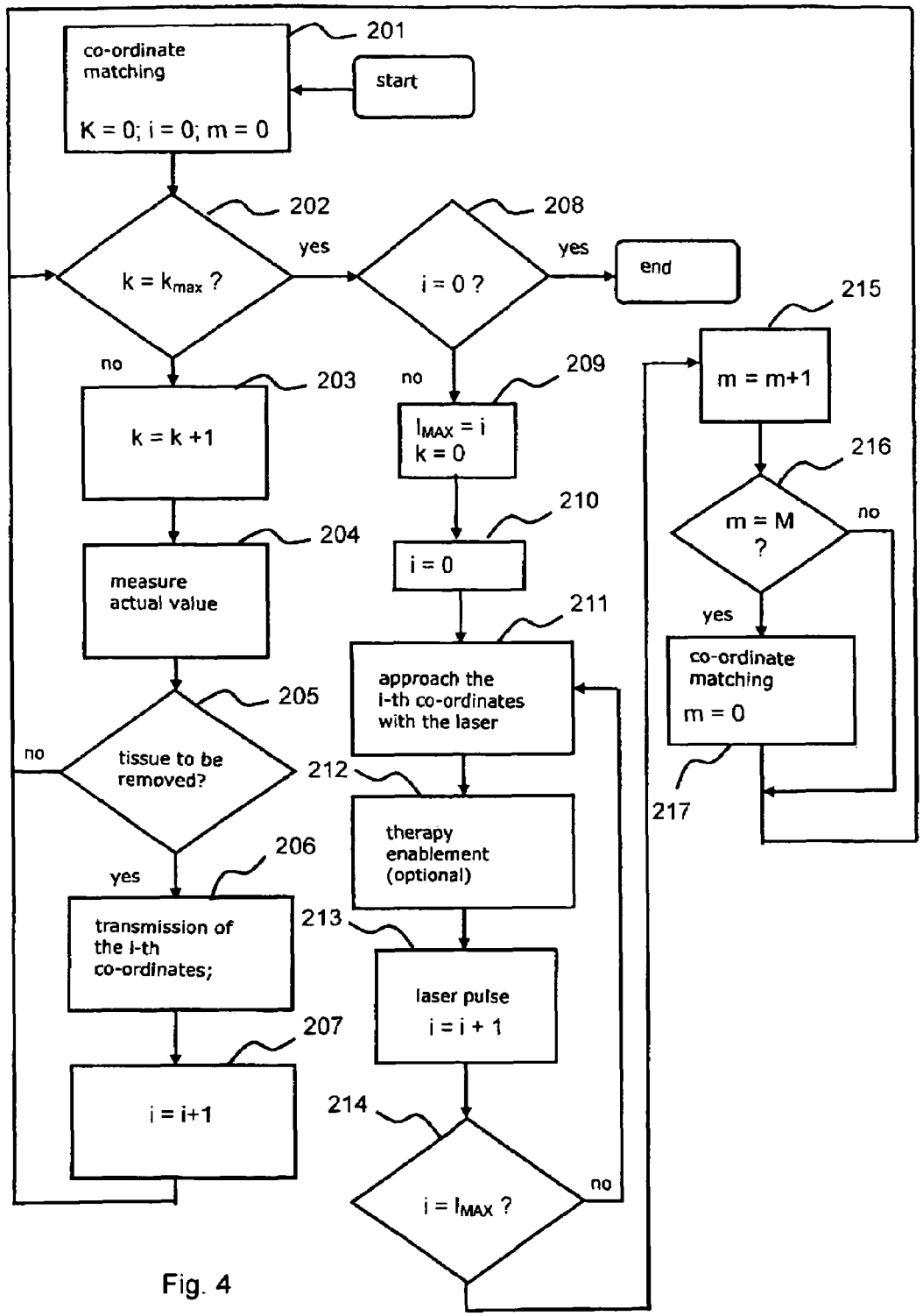
FIG. 4 shows a second possible procedure for effecting treatment with the apparatus according to the invention by means of a flow chart.

A second possible procedure for a treatment with the apparatus according to the invention for the treatment of body tissue is set forth hereinafter with reference to the flow chart in FIG. 4, in regard to the removal of body tissue. In this procedure also the actual value in respect of the body tissue is measured in a region of the body, which is represented by k measuring points. In contrast to the procedure described with reference to FIG. 3 however, the treatment with laser pulses takes place only when the actual values of all $k_{max}$ measuring points have been measured.

At the beginning of the treatment, an initialisation step 201 is effected, in which the co-ordinate system of the operating instrument 1 is matched to the co-ordinate system of the patient 31 and all relevant parameters are set to a start value. The next step 202 involves querying whether the actual value has been measured at all k measuring points. If that is not the case the value of k is increased by one in the following step 203, whereupon measurement of the actual value in respect of the parameter at the k+1-th measuring point follows in step 204. If the identifier does not detect any body tissue to be removed in step 205, the apparatus returns to step 202.

If the identifier in contrast identifies tissue to be removed at the k+1-th measuring point, then firstly in step 206 the co-ordinates of the measuring point are transmitted to a memory 17 which is present in the positioning device 2 or an external memory 17 which is connected thereto, and in step 207 i is increased by one before the apparatus returns to step 202. Steps 202 to 205 and 207 respectively are repeated until the actual values are measured at all measuring points, that is to say k has reached the value $k_{max}$.

After $k_{max}$ is reached, step 208 entails checking whether i is of the value zero. If that is the case no tissue to be removed has been identified in the whole region of tissue. Accordingly, no co-ordinates were transmitted to the memory 17 of the positioning device 2. In this case the apparatus terminates the treatment.

If however in step 208 i is of a value that is different from zero, that means that tissue to be removed has been identified at at least one measuring point. The apparatus then progresses to step 209 in which a parameter $I_{max}$ receives the current value of i and k is reset to zero. In subsequent step 210 i is then also reset to zero.

In step 211 the positioning device 2 moves to the measuring point represented by the i-th co-ordinates (at which tissue to be removed has been identified in step 205). After an optional step 212 of therapy enablement by the doctor, in step 213 a laser pulse is delivered to the tissue to be removed and the value i is increased by one.

Step 214 involves running a check to ascertain whether i has reached the value $I_{max}$, that is to say whether all co-ordinates transmitted in step 206 have been approached and the corresponding tissue regions have been treated with a laser pulse. If that is not the case the apparatus returns to step 211 and approaches the i+1-th co-ordinates. Steps 211 to 214 are repeated until all co-ordinates at which tissue to be removed has been identified in step 205 have been treated with a laser pulse.

As soon as it is established in step 214 that i has reached the value $I_{max}$, the value of the parameter m which counts how often the treatment has already been effected in accordance with steps 209 to 214 is increased by one in step 215.

Step 216 then entails checking whether a predetermined maximum value M for m is reached. If so, step 217 involves implementing a renewed matching of the co-ordinate system of the operating instrument 1 to that of the patient 31. If in contrast the maximum value M has not yet been reached, step 217 is omitted. The apparatus then returns to step 202.

Step 202 then involves establishing that k has not yet reached the value $k_{max}$ as k has been previously set to zero in step 209. Checking of the tissue for tissue to be removed on the basis of steps 202 to 207 and optionally the treatment in accordance with steps 209 to 214 are then effected again, more specifically, until the identifier 4 no longer identifies tissue to be removed, in steps 202 to 205. The latter signifies that i is of the value zero as i was reset to zero in step 210 and also steps 206 and 207 were not executed, in the absence of identified tissue to be removed. As soon as it is established in step 202 that $k_{max}$ has been reached, step 208 involves establishing that i is of the value zero, whereupon the treatment is concluded.

Instead of operating with only one laser pulse, it is also possible to effect a respective treatment with a plurality of laser pulses in step 213 in the procedure described with reference to FIG. 4.

Instead of being designed for the removal of body tissue the laser can also be designed for radiation treatment of the body tissue.

A laser is referred to as the treatment or operating instrument in the apparatus for the removal of body tissue, which has been described with reference to FIGS. 1 and 2. It is however also possible to use other treatment or operating instruments. At this juncture, mention may be made of the pulsed bipolar plasma scalpel (PEAK—Pulsed Electron Avalanche Knife) as a possible treatment instrument. Such a scalpel produces in conducting media plasma currents and microexplosions which mechanically destroy the tissue. In that respect thermal effects are negligible because of the short pulse duration. The removal of body tissue with low levels of collateral damage is possible with the PEAK.

Measurement of the tissue parameter also does not need to be effected by means of optical coherence tomography, as described hereinbefore. Alternatives are for example measuring apparatuses and methods which are based on fluorescence spectroscopy or inline microscopy. It is also possible to use optical apparatuses. The tissue parameter can then be ascertained for example on the basis of the optically obtained image by means of various threshold values in respect of colour and/or intensity.

The invention claimed is:

1. An apparatus for the treatment of body tissue comprising
    a treatment instrument for the treatment of the body tissue to be treated, the treatment instrument being adapted to deliver treatment energy in pulse form;
    a measuring unit for measuring the actual value of a parameter of the body tissue at at least one measuring point of the body tissue;
    an identifier connected to the measuring unit for identifying the body tissue to be treated on the basis of the actual value and for outputting a co-ordinate signal containing the co-ordinates of the body tissue to be treated;
    a positioning device connected to the identifier for receiving the co-ordinate signal for moving to the body tissue to be treated with the treatment instrument on the basis of the co-ordinate signal;
    an activator for activating the treatment instrument;
    a matching device for matching the co-ordinate system of the body tissue to be treated and the co-ordinate system of the treatment instrument; and
    an updating device which is connected to the measuring unit, to the identifier and to the matching device, the updating device including at least one counter for counting the pulses delivered by the treatment instrument and being adapted to output an updating signal after a first given number of delivered pulses (N) to the measuring unit for triggering renewed measurement of the actual value and to the identifier for renewed identification of body tissue to be treated based on the renewed measurement, the identifier outputting a renewed coordinate signal to the positioning device for effecting treatment and the updating device further adapted for the repeated delivery of a matching signal after a second given number of delivered pulses (M) to the matching device for re-triggering co-ordinate system matching of co-ordinate system of the body tissue to the co-ordinate system of the treatment instrument to reduce displacement of the two co-ordinate systems to each other.

2. The apparatus of claim 1 in which the identifier includes a memory for the storage of at least one reference value in respect of the parameter and a comparison device connected to the memory and the measuring unit for comparing the actual value to the at least one reference value, and in which the identifier is adapted to output the co-ordinate signal when the comparison operation produces predetermined result.

3. The apparatus of claim 2 in which the comparison device is adapted to output an identification signal identifying the body tissue to be treated and in which the identifier includes a co-ordinate detection unit connected to the comparison device for reception of the identification signal for detecting the co-ordinates of the tissue to be treated upon reception of the identification signal and for outputting the co-ordinate signal.

4. The apparatus of claim 3 in which the co-ordinate detection unit is adapted for emitting a plurality of co-ordinates respectively representative of body tissue to be treated in a co-ordinate signal and the positioning device is adapted for successively approaching the body tissue to be treated and represented by the co-ordinates with the treatment instrument.

5. The apparatus of claim 1 in which the treatment instrument is a laser.

6. The apparatus of claim 1 in which the treatment instrument is a pulsed bipolar plasma scalpel.

7. The apparatus of claim 1 in which the measuring unit is based on fluorescence measurement, optical coherence tomography, inline microscopy or an optical image.

8. The apparatus of claim 1 comprising an enablement device for enablement of the treatment instrument.

9. Apparatus for the treatment of body tissue comprising:
a laser or PEAK for the treatment of the body tissue to be treated, the laser or PEAK being adapted to deliver treatment energy in pulse form;
a fluorescence measurement unit, an optical coherence tomography unit, an inline microscopy unit or an optical imaging unit as a measuring unit for measuring the actual value of a parameter of the body tissue at at least one measuring point of the body tissue;
a memory containing at least one reference value in respect of the parameter of the body tissue;
a comparator connected to the measuring unit for receiving the actual value of the body tissue and connected to the memory for receiving the reference value, the comparator being adapted for comparing the actual value of the body tissue with the reference value and for outputting an identification signal if the comparison reveals that the actual value of the body tissue and the reference value are in a predetermined relationship;
a co-ordinate detection device connected to the comparator for detecting, upon receiving an identification signal from the comparator, the co-ordinates of the measuring point at which the actual parameter is measured and for outputting a co-ordinate signal containing the co-ordinates of the body tissue to be treated;
a support stand being adapted for positioning the laser or PEAK and being connected to the co-ordinate detection device for receiving the co-ordinate signal for moving to the body tissue to be treated with the laser or PEAK on the basis of the co-ordinate signal;
an activator for activating the treatment instrument;
a matching device for matching the co-ordinate systems of the body tissue to be treated and the co-ordinate system of the treatment instrument; and
an updating device which is connected to the measuring unit, to the comparator and to the matching device, the updating device including at least one counter for counting the pulses delivered by the laser or PEAK and being adapted to output an updating signal after a first given number of delivered pulses (N) to the measuring unit for triggering renewed measurement of the actual value and to the comparison unit for renewed comparison of body tissue to be treated based on the renewed measurement, the comparator outputting a renewed identification signal for effecting treatment and the updating device further adapted for repeated delivery of a matching signal after a second given number of delivered pulses (M) for re-triggering co-ordinate system matching of the co-ordinate system of the body tissue to the co-ordinate system of the treatment instrument to reduce displacement of the two co-ordinate systems to each other.

10. A method for treating body tissue comprising the steps of:
a) measuring an actual value of a parameter of the body tissue by an online recognition method at at least one measuring point;
b) identifying body tissue to be treated on the basis of the measured actual value of the parameter of the body tissue;
c) establishing co-ordinates of the body tissue which has been identified to be treated and using those co-ordinates for automated positioning of a treatment instrument;
d) treating the body tissue which has been identified with the treating instrument;
e) repeating steps a) through d) until no more body tissue to be treated is identified;
wherein after a predetermined number of iterations of steps a) through d), matching the co-ordinate system of the body tissue to be treated to the co-ordinate system of the treatment instrument to reduce displacement of the two coordinate systems to each other.

* * * * *